United States Patent
Markovits Rojas et al.

(10) Patent No.: US 10,836,701 B2
(45) Date of Patent: Nov. 17, 2020

(54) FISH OIL CHOLESTEROL

(71) Applicants: Alejandro Markovits Rojas, Santiago (CL); Steven Lee Härting Eckman, Santiago (CL); Thomas Francis Härting Glade, Santiago (CL)

(72) Inventors: Alejandro Markovits Rojas, Santiago (CL); Steven Lee Härting Eckman, Santiago (CL); Thomas Francis Härting Glade, Santiago (CL)

(*) Notice: Subject to any disclaimer, the term of this patent is extended or adjusted under 35 U.S.C. 154(b) by 0 days.

(21) Appl. No.: 16/830,990

(22) Filed: Mar. 26, 2020

(65) Prior Publication Data
US 2020/0317597 A1    Oct. 8, 2020

Related U.S. Application Data

(60) Provisional application No. 62/829,374, filed on Apr. 4, 2019.

(51) Int. Cl.
    *C07C 51/44*      (2006.01)
    *C07J 9/00*      (2006.01)

(52) U.S. Cl.
    CPC ............. *C07C 51/44* (2013.01); *C07J 9/00* (2013.01)

(58) Field of Classification Search
    CPC .................. C07C 51/44; C07J 9/00
    USPC ............................................. 540/2
See application file for complete search history.

(56) References Cited

U.S. PATENT DOCUMENTS

| | | | |
|---|---|---|---|
| 6,846,941 B2 * | 1/2005 | Rohr | C11C 1/025 554/195 |
| 7,678,930 B2 | 3/2010 | Sondbo et al. | |
| 7,718,698 B2 | 5/2010 | Breivik et al. | |
| 8,258,330 B1 | 9/2012 | Harting Glade et al. | |
| 10,196,583 B1 | 2/2019 | Markovits Rojas et al. | |

FOREIGN PATENT DOCUMENTS

| | | |
|---|---|---|
| WO | 2016/096989 A1 | 6/2016 |
| WO | 2019/053744 A1 | 3/2019 |

OTHER PUBLICATIONS

Larssen, W.E. et al., "Sensory description of marine oils through development of a sensory wheel and vocabulary", Food Research International, 106: 45-53 (2018).

* cited by examiner

*Primary Examiner* — Deborah D Carr
(74) *Attorney, Agent, or Firm* — Merchant & Gould P.C.

(57) ABSTRACT

The present disclosure describes that high purity cholesterol is obtained by the processes of the invention without any further purification step, such as a crystallizing step from a solvent, but rather by distilling steps alone. The disclosures provides a process that includes the production of compositions having a cholesterol content over 75% in weight, from fish oil processing waste residues.

16 Claims, 1 Drawing Sheet

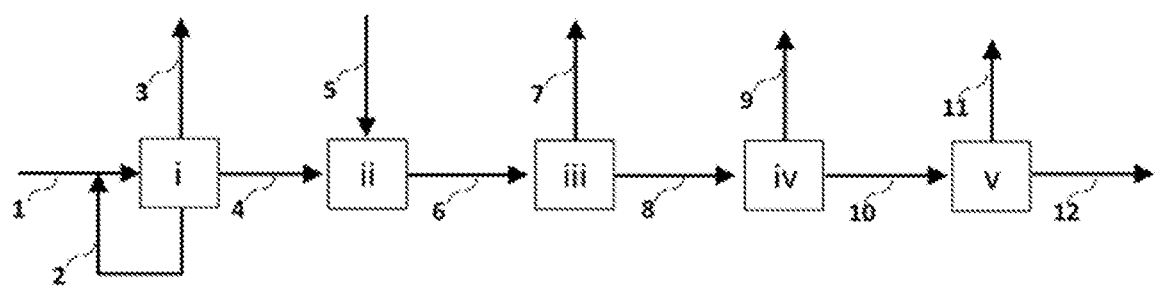

FISH OIL CHOLESTEROL

CROSS-REFERENCE TO RELATED APPLICATION

This application claims benefit of U.S. Patent Application Ser. No. 62/829,374, filed 4 Apr. 2019, and which application is incorporated herein by reference. A claim of priority is made to the above-disclosed application.

BACKGROUND OF THE INVENTION

1. Field of the Invention

This invention relates to processes for the production of compositions having a cholesterol content over 75% in weight, from fish oil processing waste residues.

Background

U.S. Pat. No. 10,196,583 (Markovits and Härting "Fish Oil Cholesterol") discloses a process for the production from fish oil of a pharmaceutical grade cholesterol. A disadvantage of the process disclosed resides in the use of solvents for separating cholesterol from fatty acid soaps. The solvents or solvent mixtures are used in very large proportions, when compared to the quantity of material submitted for extraction, and the solvents need additional processes for their removal and/or recycling in the extraction and pre-concentration process of the valuable products. In addition, if solvent mixtures are utilized, the cost of recovery and recycling increases excessively. The foregoing reasons make solvent-based processes expensive, and lead to an expensive final product. In addition, the yield of cholesterol recovery from fish oil is generally less than 70%.

U.S. Pat. No. 6,846,941 (Resitec Industria Quimica Ltda. "Process for separating non-saponifiable valuable products from raw materials") discloses a process wherein valuable non-saponifiable materials are separated from a large variety of raw materials of animal or vegetable origin as well as from by-products, residues, and waste products from the processing of animal or vegetable products, such as from food processing, cellulose processing and the like. In case fish oil was the raw material, the valuable non-saponifiable material is cholesterol. The process comprises saponifying the raw material with sodium or potassium hydroxide, converting the sodium or potassium soaps into metallic soaps, like magnesium or zinc soaps for example, the distilling the mixture of metallic soaps, wherein the distillate, in the case the starting material is fish oil, comprise cholesterol and the residue comprising metallic soaps.

The reasons to convert alkali soaps to metallic soaps, according to the inventors, arise from the problems and difficulties in the distilling of the alkali saponified mixture.

The process of U.S. Pat. No. 6,846,941 has several disadvantages, especially when the starting material is fish oil, among them: the separation of cholesterol leads to the transformation of valuable fish oil into metallic soaps; the cholesterol distillate comprises most of toxic and/or harmful anthropogenic contaminants (POPs) of the fish oil; and the obtaining of cholesterol of high purity, 65% or higher, requires a further crystallization of the cholesterol distillate.

WO2016096989 disclose a process for extracting cholesterol from fish oil waste residue by saponification in presence of NaOH/KOH followed by extraction with at least one non-water miscible solvent such as aliphatic or aromatic hydrocarbon at temperature above 30° C. The process involves repeated solvent extractions, crystallization and back washes to extract cholesterol. The process described in WO '989 is multistep cumbersome solvent extraction process that requires large volume of solvents.

WO 2019/053744 A1 also discloses a process for extracting cholesterol from fish oil waste residue by saponification with NaOH in presence of the catalyst 4-dimethylaminopyridine (DMAP) followed by neutralization with aqueous acid to obtain ester free cholesterol, heating the saponified mass in 2-butanone (methyl ethyl ketone) with calcium bromide to obtain cholesterol adduct, separating cholesterol from the adduct with toluene, evaporating the toluene, dissolving the cholesterol in methanol followed by crystallization of the solution to obtain cholesterol. One disadvantage of the process disclosed resides in the use of different solvents for separating cholesterol, for example methanol, 2-butanonal, toluene. The solvents are used in large proportions and additional processes are needed for their removal and/or recycling in the extraction and pre-concentration process of the valuable products. In addition, the cost of recovery and recycling increases excessively. Another disadvantage is the use of 4-dimethylaminopyridine (DMAP). DMAP has a relatively high toxicity and is particularly dangerous because of its ability to be absorbed through the skin. Finally, the process generates a high amount of waste stream residues.

SUMMARY OF THE INVENTION

Embodiments of the present disclosure provide processes for the production from fish oil processing waste residues, compositions having a cholesterol content over 75% in weight.

The compositions obtained by the disclosed processes are suitable as additive to shrimp and prawn feed in aquaculture, as well as for the production of vitamins $D_2$, $D_3$, hormones and as emulsifying agent of W/O emulsions in cosmetics and pharmaceutical formulations.

As used herein, the term "fish oil processing waste residues" comprise the distillate or the vacuum stripped fraction of fish oil for reducing the content of environmental pollutants in fish oil as disclosed, for example, in U.S. Pat. Nos. 8,258,330 and 7,718,698, wherein such stripped fractions comprise cholesterol as well, or the vacuum stripped fraction of fish oil for reducing the content of cholesterol in fish oil as disclosed in U.S. Pat. No. 7,678,930, wherein such stripped fractions comprise typically from 5-15% of cholesterol, together with the environmental pollutants of fish oil. Evidently, the major part of these fractions consist of the fluid utilized for the stripping process, most frequently one or more ethyl esters of fatty acids. If desired, such stripped fraction may be bleached with bleaching clay, activated carbon or with other bleaching agents. This kind of residue from here onwards is referred to as "light waste residue".

Fish oil processing waste residue also comprise the final residue or the residue from the last step of a two or more multistep short path/molecular distillation process for the manufacture of omega-3 concentrates from fish oils transesterified with ethanol. The yield of transesterification of fish oils is usually less than 95% which leads to the presence of partial glycerides in the final residue of the multistep short path distillation process. The final residue is a fish oil waste residue containing typically between 5-25% of cholesterol, either as free cholesterol or esterified cholesterol, and other high boiling fractions of the transesterified fish oil, among them mono and diglycerides of fatty acids from $C_{18}$ to $C_{22}$ omega-3 fatty acids like EPA, DHA and DPA (22:5n3) as well as minor quantities of partial glycerides of polyunsaturated fatty acids having over $C_{18}$ carbon atoms. U.S. Pat. No. 10,050,704 describes the process of obtaining the final residue of a typical two step short path/molecular distillation process for the manufacture of omega-3 concentrates from fish oils transesterified with ethanol. If desired such final residue may be bleached with bleaching clay, activated carbon or other bleaching agents. This kind of residue from here onwards is referred to as "heavy waste residue".

Therefore, as used herein the term "fish oil processing waste residues" include the "light waste residue" or the "heavy waste residue" or any mixture of both residues.

In one aspect, the disclosed embodiments relate to a process for producing from fish oil processing waste residues a composition comprising cholesterol, the process comprising the following steps: (a) contacting a fish oil processing waste residue with an alkali to obtain a saponified mixture, (b) subjecting the saponified mixture to a distillation step to obtain a first distillate and a first residue, (c) subjecting the first residue to a vacuum distillation step to obtain a second distillate and a second residue, and (d) subjecting the second residue to a vacuum distillation step to obtain a third distillate and a third residue, wherein the third distillate is a composition comprising at least 75% in weight of cholesterol.

In an embodiment, the alkali in step (a) is NaOH or KOH, preferably NaOH and most preferably an aqueous solution of NaOH. In another embodiment, in step (a) fish oil processing waste residue is contacted with an alkali such as NaOH or KOH in a solution comprising water and a polar solvent such as methanol or ethanol or a mixture of said solvents. In another embodiment, the alkali in step (a) is contacted with the fish oil processing waste residue in a pressurized stirred reactor. In another embodiment, the alkali in step (a) is contacted with the fish oil processing waste residue during a time interval from 1 to 120 minutes. In another embodiment, the alkali in step (a) is contacted with the fish oil processing waste residue at a temperature interval of 50 to 200° C. In another embodiment the alkali in step (a) is contacted with the fish oil processing waste residue at a pressure interval of 1 to 20 bar. In a preferred embodiment the alkali in step (a) is contacted with the fish oil processing waste residue in a pressurized stirred reactor during a time interval from 1 to 120 minutes, temperature in the interval of 50 to 200° C. and pressure in interval of 1 to 20 bar.

In another embodiment, step (b) is carried out in a short path distillation column or a molecular distillation column or a thin film distillation column. In another embodiment, the saponified mixture feed flow rate in step (b) is in the interval of 10-350 kg/h/m². In another embodiment, the temperature in step (b) is in the interval of 150-400° C. In another embodiment, the pressure in step (b) is below 2 bar. In a preferred embodiment step (b) is carried out in a short path distillation column, the saponified mixture feed flow rate is in the interval of 10-350 kg/h/m², the temperature is in the interval of 150-400° C. and the pressure is below 2 bar.

In another embodiment, step (c) is carried out in a short path distillation column or a molecular distillation column. In another embodiment the first residue feed flow rate in step (c) is in the interval of 10-350 kg/h/m². In another embodiment, the temperature in step (c) is in the interval of 200-400° C. In another embodiment, the pressure in step (c) is below 500 mbar. In a preferred embodiment step (c) is carried out in a short path distillation column, the first residue feed flow rate is in the interval of 10-350 kg/h/m², the temperature is in the interval of 200-400° C., and the pressure is below 500 mbar.

In another embodiment, step (d) is carried out in a short path distillation column or a molecular distillation column. In another embodiment the second residue feed flow rate in step (d) is in the interval of 10-350 kg/h/m². In another embodiment, the temperature in step (d) is in the interval of 200-400° C. In another embodiment, the pressure in step (d) is below 10 mbar. In a most preferred embodiment of the invention, step (d) is carried out in a short path distillation column, the second residue feed flow rate is in the interval of 10-350 kg/h/m², the operating temperature is in the interval of 200-400° C. and the pressure is below 10 mbar.

In another aspect, the disclosed embodiments relate to a process for producing from fish oil processing waste residues a composition comprising cholesterol, the process comprising the following steps: (i) vacuum distilling the fish oil processing waste residue to obtain a first distillate and a first residue, (ii) contacting the first residue with an alkali to obtain a saponified mixture (iii) subjecting the saponified mixture to a distillation step to obtain a second distillate and a second residue, (iv) subjecting the second residue to a vacuum distillation step to obtain a third distillate and a third residue, and (v) subjecting the third residue to a vacuum distillation step to obtain a fourth distillate and a fourth residue, wherein the fourth distillate is a composition comprising at least 75% in weight of cholesterol In an embodiment, the alkali in step (ii) is NaOH or KOH, preferably NaOH and most preferably an aqueous solution of NaOH. In another embodiment, in step (ii) the first residue is contacted with an alkali such as NaOH or KOH in a solution comprising water and a polar solvent such as methanol or ethanol or a mixture of said solvents. In another embodiment, the alkali in step (ii) is contacted with the first residue in a pressurized stirred reactor. In another embodiment, the alkali in step (ii) is contacted with the first residue during a time interval from 1 to 120 minutes. In another embodiment, the alkali in step (ii) is contacted with the first residue at a temperature interval of 50 to 200° C. In another embodiment the alkali in step (ii) is contacted with the first residue at a pressure interval of 1 to 20 bar. In a preferred embodiment the alkali in step (ii) is contacted with the first residue in a pressurized stirred reactor during a time interval from 1 to 120 minutes, temperature in the interval of 50 to 200° C. and pressure in interval of 1 to 20 bar.

In another embodiment, step (iii) is carried out in a short path distillation column or a molecular distillation column or a thin film distillation column. In another embodiment, the saponified mixture feed flow rate in step (iii) is in the interval of 10-350 kg/h/m². In another embodiment, the temperature in step (iii) is in the interval of 150-400° C. In another embodiment, the pressure in step (iii) is below 2 bar. In a preferred embodiment step (iii) is carried out in a short path distillation column, the saponified mixture feed flow rate is in the interval of 10-350 kg/h/m², the temperature is in the interval of 150-400° C. and the pressure is below 2 bar.

In another embodiment, step (iv) is carried out in a short path distillation column or a molecular distillation column. In another embodiment the second residue feed flow rate in step (c) is in the interval of 10-350 kg/h/m². In another embodiment, the temperature in step (c) is in the interval of 200-400° C. In another embodiment, the pressure in step (iv) is below 500 mbar. In a preferred embodiment step (iv) is carried out in a short path distillation column, the second residue feed flow rate is in the interval of 10-350 kg/h/m², the temperature is in the interval of 200-400° C., and the pressure is below 500 mbar.

In another embodiment, step (v) is carried out in a short path distillation column or a molecular distillation column. In another embodiment the third residue feed flow rate in step (v) is in the interval of 10-350 kg/h/m$^2$. In another embodiment, the temperature in step (d) is in the interval of 200-400° C. In another embodiment, the pressure in step (v) is below 10 mbar. In a most preferred embodiment of the invention, step (v) is carried out in a short path distillation column, the third residue feed flow rate is in the interval of 10-350 kg/h/m$^2$, the operating temperature is in the interval of 200-400° C. and the pressure is below 10 mbar In another embodiment, step (i) is carried out in a short path distillation column or a molecular distillation column. In another embodiment the fish oil processing waste residue feed flow rate in step (i) is in the interval of 10-350 kg/h/m$^2$. In another embodiment, the operating temperature in step (a) is in the interval of 100-250° C. In another embodiment, the pressure in step (i) is below 0.5 mbar. In a preferred embodiment, step (i) is carried out in a short path distillation column fish oil processing waste residue feed flow rate is in the interval of 10-350 kg/h/m$^2$, the temperature is in the interval of 100-250° C. and the pressure is below 0.5 mbar. In a most preferred embodiment, step (a) is carried out in dual distillate short path evaporator wherein the lower distillate fraction collected at the bottom of the internal condenser is contacted with the fish oil processing waste residue fed to the column in step (i).

A short path distillation column also known as short path evaporator typically includes a vertical cylindrical body or column with a heating jacket, a rotor and a condenser inside close to the heated surface. On the supporting structure of the rotor mobile precision wiper blades are mounted, which pump and agitate the feed material down the heated wall. Evaporation takes place from the heated wiped film. As the feed enters the cylinder, it encounters rotating wipers or rollers that create a thin film on the heated surface. A condenser in the middle of the apparatus, cooled with a cooling fluid, condenses the distillate. Receiving vessels collect the distillate and the high temperature residue at the bottom. Some short path distillation columns also comprise a distillate collecting tray concentric with the condenser, located at a certain high along the condenser. This design allows the separation of the distillate in two fractions; one fraction condensing in the section above the collecting dish, comprising the higher vapor pressure components of the mixture subjected to distillation, referred to as "the upper condensate" this point onwards, and an another fraction condensing below the collecting tray comprising the lower vapor pressure components of the mixture subjected to distillation referred to as "the lower condensate" this point onwards. Both fractions are withdrawn separately from the column. Such columns are known as dual distillate short path evaporators (DD-SPE).

The distillation operating conditions comprise the column temperature, pressure and feed flow rate and refer to the temperature of the heated surface, the column pressure and feed flow rate (mass/time/heated surface area) entering the top of the column.

The short path distillation column is also known as a molecular distillation column when the distance between the heated surface of the distillation column and the internal condenser surface is comparable to the mean free path of the distillate molecules under the operating conditions, therefore in some embodiments short path distillation and molecular distillation mean that the distillation is carried out in a distillation column which has an internal condenser at the proximity of the heated surface of the distillation column. A thin film distillation column is a distillation column, which has an external condenser. A distillation column is also referred to as an evaporator.

DETAILED DESCRIPTION OF THE INVENTION

It is a surprising and unexpected feature common to embodiments of the present disclosure that high purity cholesterol is obtained by the processes of the present invention without any further purification step, such as a crystallizing step from a solvent, but rather by distilling steps alone. Table A below shows sterol yields and purities, without a crystallizing step as shown in U.S. Pat. No. 6,846,941, and of the processes of the present disclosure.

TABLE A

| | Sterol yields and purities without a crystallizing step. | | | | |
|---|---|---|---|---|---|
| | Fish oil waste residues (Present invention) | TOP (tall oil pitch) | DDOS (deodorizer distillate of soya) | BLSS* (black liquor soap skimmings) | CTO (crude tall oil) |
| Yield (%) | 75-95 | 80-90 | 75-85 | 70-85 | 80-90 |
| Purity (%) | Over 75 | Less than 65 | Less than 35 | Less than 50 | Less than 50 |

*the skim soap residue of the Kraft sulfate paper pulping process.

It is as well, an advantageous feature common to embodiments of the present disclosure that in addition to high purity cholesterol, a valuable by-product in the form of omega-3 fatty acids are obtained as well.

In some embodiments of the present disclosure provide a process for producing a composition comprising cholesterol from fish oil processing waste residues. The process comprising of the steps:
  (a) contacting a fish oil processing waste residue with an alkali to obtain a saponified mixture,
  (b) subjecting the saponified mixture to a distillation step to obtain a first distillate and a first residue,
  (c) subjecting the first residue to a vacuum distillation step to obtain a second distillate and a second residue, and
  (d) subjecting the second residue to a vacuum distillation step to obtain a third distillate and a third residue, wherein the third distillate is a composition comprising over 75% in weight of cholesterol.

In some embodiments a process for producing a composition comprising cholesterol from fish oil processing waste residues. The process comprising of the steps:
  (i) vacuum distilling the fish oil processing waste residue to obtain a first distillate and a first residue,
  (ii) contacting the first residue with an alkali to obtain a saponified mixture,
  (iii) subjecting the saponified mixture to a distillation step to obtain a second distillate and a second residue, (iv) subjecting the second residue to a vacuum distillation step to obtain a third distillate and a third residue, and (v) subjecting the third residue to a vacuum distillation step to obtain a fourth distillate and a fourth residue, wherein the fourth distillate is a composition comprising over 75% in weight of cholesterol.

Step (a).

In some embodiments, the fish oil processing waste residue is contacted with an alkali comprising an aqueous solution of NaOH or KOH to form a saponified mixture in a step (a). The weight ratio of the fish oil processing waste residue to the aqueous solution of alkali is from 1:0.01 to 1:1, preferably from 1:0.1 to 1:0.3. Alternatively, the fish oil processing waste residue is contacted with an alkali such as NaOH or KOH in a solution comprising water and a polar solvent such as methanol or ethanol or any mixture of said solvents to form a saponified mixture. In some embodiments, the weight ratio of the fish oil processing waste residue to the solution is from 1:0.01 to 1:1, preferably from 1:0.1 to 1:0.5.

In some embodiments, the amount of alkali in the water or solution is equal to the saponification value of the fish oil processing waste residue, preferably from 0.9 to 1.2 times the saponification value of the first distillate, most preferably from 0.97 to 1.05 times the saponification value of the fish oil processing waste residue.

In some embodiments, the saponification reaction to form a saponified mixture is carried out by contacting the fish oil processing waste residue with the alkali in a stirred closed vessel or in a continuous reactor during 1 to 120 minutes, preferably 2 to 30 minutes at temperature from 50 to 200° C., preferably from 100 to 180° C. and the pressure from 1 to 20 bar, preferably from 2 to 10 bar.

Step (b).

In some embodiments, following step (a), the saponified mixture is distilled in step (b). In one embodiment, step (b) is carried out in a short path distillation column or a molecular distillation column or in a thin film distillation column. In another embodiment the saponified mixture feed flow rate is in the interval of 10-350 kg/h/m$^2$, preferably in the interval of 75-220 kg/h/m$^2$. In another embodiment, the temperature in step (b) is in the interval of 150-400° C., preferably in the interval of 200-300° C. In another embodiment, the pressure in step (b) is below 2 bar, preferably in the interval of 0.5 to 1.5 bar. In a preferred embodiment, step (b) is carried out in a short path distillation column and the saponified mixture feed flow rate is in the interval of 10-350 kg/h/m$^2$, the temperature is in the interval of 150-400° C. and the pressure is below 2 bar. In another preferred embodiment, step (b) is carried out in a short path distillation column, the saponified mixture feed flow rate is in the interval of 75-220 kg/h/m$^2$, the temperature is in the interval of 200-300° C. and the pressure is in the interval of 0.5 to 1.5 bar.

In some embodiments, the distillation process of step (b) results in the separation of a first distillate and a first residue, which leave the distillation column separately.

Step (c).

In some embodiments, following step (b), the first residue is distilled in step (c). In one embodiment, step (c) is carried out in a short path distillation column or a molecular distillation column. In another embodiment the first residue feed flow rate in step (c) is in the interval of 10-350 kg/h/m$^2$, preferably in the interval of 75-220 kg/h/m$^2$. In another embodiment, the temperature in step (c) is in the interval of 200-400° C., preferably in the interval of 250 to 350° C. In another embodiment, the pressure in step (c) is below 500 mbar, preferably at the interval of 1-100 mbar. In a preferred embodiment, step (c) is carried out in a short path distillation column and the first residue feed flow rate is at the interval of 10-350 kg/h/m$^2$, the temperature is in the interval of 200-400° C., and the pressure is below 500 mbar. In another preferred embodiment, step (c) is carried out in a short path distillation column, the first residue feed flow rate is in the interval of 75-200 kg/h/m$^2$, the temperature is in the interval of 250-350° C. and the pressure is in the interval of 1-100 mbar. Alternatively, in another embodiment step (c) can be carried out in a flash tank at a pressure below 500 mbar.

In some embodiments, the distillation process of step (c) results in the separation of a second distillate and a second residue, which leave the distillation column separately.

Step (d).

In some embodiments, following step (c), the second residue is distilled in a step (d) to obtain a third distillate and a third residue. In some embodiments, the third distillate comprises over 75% in weight of cholesterol. In one embodiment, step (d) is carried out in a short path distillation column or a molecular distillation column. In another embodiment the second residue feed flow rate is in the interval of 10-350 kg/h/m$^2$, preferably in the interval of 75-220 kg/h/m$^2$. In another embodiment, the operating temperature of step (d) is in the interval of 200-400° C., preferably in the interval of 280 to 380° C. In another embodiment, the pressure in step (d) is below 10 mbar, preferably in the interval of 0.001-1 mbar. In a preferred embodiment, step (d) is carried out in a short path distillation column, the second residue feed flow rate is in the interval of 10-350 kg/h/m$^2$, the temperature is in the interval of 200-400° C. and the pressure is below 10 mbar. In another preferred embodiment, step (d) is carried out in a short path distillation column, the second residue feed flow rate is in the interval of 75-220 kg/h/m$^2$, the temperature is in the interval of 280-380° C. and the pressure is in the interval 0.001-1 mbar.

In some embodiments, the distillation process of step (d) results in the separation of a third distillate and a third residue, which leave the distillation column separately.

In some embodiments the third distillate from step (d) is subjected to prilling also known as spray congealing, spray chilling or melt atomization to obtain cholesterol prills or beads.

In at least one particular embodiment, a composition comprising over 96% of cholesterol can be obtained by crystallizing the third distillate in a suitable solvent or solvent mixture such as hexane, methanol, ethanol, acetone, water or mixtures thereof. In another particular embodiment, a composition comprising over 96% of cholesterol can be obtained by high vacuum fractionation of the third distillate form step (d), in a packed column distillation unit. In another particular embodiment, a composition comprising over 99% of cholesterol can be obtained by fractionating the composition of the third distillate obtained in step (d) under high pressure liquid chromatography.

In some embodiment the third residue from step (d) is acidified with a mineral acid to form a composition comprising from 10 to 70% in weight of omega-3 fatty acids said composition comprising eicosapentaenoic acid (EPA), docosahexaenoic acid (DHA) and docosapentaenoic acid (DPA). In some embodiment said composition is subjected to one or more molecular distilling step to obtain a concentrate comprising from 40 to 90% of omega-3 fatty acids suitable for animal and human consumption.

In some embodiment, the composition of omega-3 fatty acids obtained upon acidifying the third residue from step (d) is esterified with ethanol to obtain a composition comprising ethyl esters of omega-3 fatty acids. In some embodiment said composition is subjected to one or more molecular distilling step to obtain a concentrate comprising from 40 to 90% ethyl esters of omega-3 fatty acids suitable for animal and human consumption.

Step (i).

In one embodiment of the present disclosure, the fish oil processing waste residue is distilled in a short path distillation column or a molecular distillation column. In another embodiment, the fish oil processing waste residue feed flow rate is in the interval of 10-350 kg/h/m$^2$, preferably in the interval of 75-220 kg/h/m$^2$. In another embodiment, the temperature in step (i) is in the interval of 100-250° C., preferably in the interval of 120-220° C. In another embodiment, the pressure in step (i) is below 0.5 mbar, preferably in the interval of 0.001 to 0.1 mbar. In another embodiment, step (i) is carried out in a short path distillation column, the fish oil processing waste residue feed flow rate is in the interval of 10-350 kg/h/m$^2$, the temperature is in the interval of 100-250° C. and the pressure is below 0.5 bar. In another embodiment step (i) is carried out in a short path distillation column, the fish oil processing waste residue feed flow rate is in the interval of 75-220 kg/h/m$^2$, the temperature is in the interval of 120-220° C. and the pressure is in the interval of 0.001-0.1 mbar. In a preferred embodiment, step (i) is carried out in dual distillate short path evaporator, wherein the lower distillate fraction collected at the bottom of the internal condenser is contacted with the fish oil processing waste residue fed to the column in step (i).

In some embodiments, the distillation process of step (i) results in the separation of a first distillate and a first residue, which leave the distillation column separately.

If desired the first residue may be bleached with bleaching clay, activated carbon or with other bleaching agents.

Step (ii).

In some embodiments, the first residue from step (i) is contacted with an alkali comprising an aqueous solution of NaOH or KOH to form a saponified mixture in a step (b). The weight ratio of the first residue to the aqueous solution of alkali is from 1:0.01 to 1:1, preferably from 1:0.05 to 1:0.3. Alternatively, the first distillate is contacted with an alkali such as NaOH or KOH in a solution comprising water and a polar solvent such as methanol or ethanol or any mixture of said solvents to form a saponified mixture. In some embodiments, the weight ratio of the first distillate to the solution is from 1:0.01 to 1:1, preferably from 1:0.05 to 1:0.5.

In some embodiments, the amount of alkali in the water or solution is equal to the saponification value of the first residue, preferably from 0.9 to 1.2 times the saponification value of the first residue, most preferably from 0.97 to 1.05 times the saponification value of the first residue.

In some embodiments, the saponification reaction to form a saponified mixture is carried out by contacting the first residue with the alkali in a stirred closed vessel or in a continuous reactor during 1 to 120 minutes, preferably 2 to 30 minutes at temperature from 50 to 200° C., preferably from 100 to 180° C. and the pressure from 1 to 20 bar, preferably from 2 to 10 bar.

Step (iii).

In some embodiments, following step (ii), the saponified mixture is distilled in step (iii). In one embodiment, step (iii) is carried out in a short path distillation column or a molecular distillation column or in a thin film distillation column. In another embodiment the saponified mixture feed flow rate is in the interval of 10-350 kg/h/m$^2$, preferably in the interval of 75-220 kg/h/m$^2$. In another embodiment, the temperature in step (iii) is in the interval of 150-400° C., preferably in the interval of 200-300° C. In another embodiment, the pressure in step (iii) is below 2 bar, preferably in the interval of 0.5 to 1.5 bar. In a preferred embodiment, step (iii) is carried out in a short path distillation column and the saponified mixture feed flow rate is in the interval of 10-350 kg/h/m$^2$, the temperature is in the interval of 150-400° C. and the pressure is below 2 bar. In another preferred embodiment, step (b) is carried out in a short path distillation column, the saponified mixture feed flow rate is in the interval of 75-220 kg/h/m$^2$, the temperature is in the interval of 200-300° C. and the pressure is in the interval of 0.5 to 1.5 bar.

In some embodiments, the distillation process of step (iii) results in the separation of a second distillate and a second residue, which leave the distillation column separately.

Step (iv).

In some embodiments, following step (iii), the second residue is distilled in step (iv). In one embodiment, step (iv) is carried out in a short path distillation column or a molecular distillation column. In another embodiment the second residue, feed flow rate in step (iv) is in the interval of 10-350 kg/h/m$^2$, preferably in the interval of 75-220 kg/h/m$^2$. In another embodiment, the temperature in step (iv) is in the interval of 200-400° C., preferably in the interval of 250 to 350° C. In another embodiment, the pressure in step (iv) is below 500 mbar, preferably at the interval of 100-1 mbar. In a preferred embodiment, step (iv) is carried out in a short path distillation column and the second residue feed flow rate is at the interval of 10-350 kg/h/m$^2$, the temperature is in the interval of 200-400° C., and the pressure is below 500 mbar. In another preferred embodiment, step (iv) is carried out in a short path distillation column, the second residue feed flow rate is in the interval of 75-200 kg/h/m$^2$, the temperature is in the interval of 250-350° C. and the pressure is in the interval of 1-100 mbar. Alternatively, in another embodiment step (iv) can be carried out in a flash tank at a pressure below 500 mbar.

In some embodiments, the distillation process of step (iv) results in the separation of a third distillate and a third residue, which leave the distillation column separately.

Step (v).

In some embodiments, following step (iv), the third residue is distilled in a step (v) to obtain a fourth distillate and a fourth residue. In some embodiments, the fourth distillate comprises over 75% in weight of cholesterol. In one embodiment, step (v) is carried out in a short path distillation column or a molecular distillation column. In another embodiment the third residue feed flow rate is in the interval of 10-350 kg/h/m$^2$, preferably in the interval of 75-220 kg/h/m$^2$. In another embodiment, the operating temperature of step (v) is in the interval of 200-400° C., preferably in the interval of 280 to 380° C. In another embodiment, the pressure in step (v) is below 10 mbar, preferably in the interval of 0.001-1 mbar. In a preferred embodiment, step (v) is carried out in a short path distillation column, the third residue feed flow rate is in the interval of 10-350 kg/h/m$^2$, the temperature is in the interval of 200-400° C. and the pressure is below 10 mbar. In another preferred embodiment, step (v) is carried out in a short path distillation column, the third residue feed flow rate is in the interval of 75-220 kg/h/m$^2$, the temperature is in the interval of 280-380° C. and the pressure is in the interval 0.001-1 mbar.

In some embodiments, the distillation process of step (v) results in the separation of a fourth distillate and a fourth residue, which leave the distillation column separately.

In some embodiments the fourth distillate from step (v) is subjected to prilling also known as spray congealing, spray chilling or melt atomization to obtain cholesterol prills or beads.

In at least one particular embodiment, a composition comprising over 96% of cholesterol can be obtained by crystallizing the fourth distillate in a suitable solvent or solvent mixture such as hexane, methanol, ethanol, acetone, water or mixtures thereof. In another particular embodiment, a composition comprising over 96% of cholesterol can be obtained by high vacuum fractionation of the third distillate form step (d), in a packed column distillation unit. In another particular embodiment, a composition comprising over 99% of cholesterol can be obtained by fractionating the composition of the fourth distillate obtained in step (v) under high pressure liquid chromatography.

In some embodiment the fourth residue from step (v) is acidified with a mineral acid to form a composition comprising from 10 to 70% in weight of omega-3 fatty acids said composition comprising eicosapentaenoic acid (EPA), docosahexaenoic acid (DHA) and docosapentaenoic acid (DPA). In some embodiment said composition is subjected to one or more molecular distilling step to obtain a concentrate comprising from 40 to 90% of omega-3 fatty acids suitable for animal and human consumption.

In some embodiment the composition of omega-3 fatty acids obtained upon acidifying the fourth residue from step (v) is esterified with ethanol to obtain a composition comprising ethyl esters of omega-3 fatty acids. In some embodiment said composition is subjected to one or more molecular distilling step to obtain a concentrate comprising from 40 to 90% ethyl esters of omega-3 fatty acids suitable for animal and human consumption.

FIG. 1 is an embodiment of a continuous process for producing a composition comprising cholesterol from fish oil processing waste residues, wherein step (i) is carried out in a dual distillate short path evaporator.

Referring to FIG. 1, where a dual distillate short path evaporator in step (i) is shown. "The lower condensate" from the dual distillate short path evaporator (i) collected through line 2 is contacted with an incoming "fish oil processes waste residue" in line 1 forming a mixture which is fed to the evaporator (i). "The upper condensate" leaving the evaporator (i) thorough line 3 is discarded. The residue of step (i), the first residue of an embodiment of the process disclosed above, leaves the column through line 4.

Through line 4, the reactor (ii) is fed with the residue and simultaneously through line 5, aqueous sodium hydroxide is feed to the reactor (ii) to form a saponified mixture which leaves the reactor through line 6.

Through line 6, the saponified mixture is fed to the short path distillation column (iii) to produce a distillate which leaves the distillation column through line 7 and a residue which leaves the column through line 8.

Through line 8, the residue is fed to the short path distillation column (iv) to produce a distillate which leaves the column through line 9 and a residue which leaves the column through line 10.

Through line 10, the residue is fed continuously to the short path distillation column (v) to produce a residue comprising fatty acid soaps that leaves the column through line 12 and a distillate, comprising cholesterol, which leaves the distillation column through line 11.

EXAMPLES

The analytical data disclosed in the examples are based on the analytical methodologies described in the European Pharmacopeia 9.0 and 9.2, which is incorporated herein by reference in its entirety.

Example 1. Process for the Production of Cholesterol from a "Light Waste Residue"

The cholesterol and environmental contaminants content of the "light waste residue" utilized in Example 1 is shown in Table 1 below:

TABLE 1

Composition of the "light weight residue" utilized in Example 1.

| | |
|---|---|
| Cholesterol, % | 9.2 |
| Dioxins, Furans and Dioxin like PCBs, TEQ ppt (upper bound) | 8.9 |
| Total PCB (209 congeners), ppb (upper bound) | 178.0 |
| Total PAH (13 PAH), ppb | 31.9 |
| 3-MCPD, ppb | 4,400 |
| Glycidol, ppb | 2,900 |
| Organochlorine Pesticides and Pyrethroides, ppm | 72.0 |
| Organophosphorus Pesticides, ppm | 17.6 |

1000 kg of the "light waste residue" was fed at the rate of 100 kg/h to an UIC short path distillation column having an evaporator surface of 1 m$^2$ and distilled at 152° C. and 0.04 mbar leading the 660 kg of a first distillate and 340 kg of a first residue. The first residue contained 24.5 wt. % of cholesterol.

150 kg of the first residue was mixed with 27 kg of an aqueous solution of NaOH (50%) in an agitated pressure reactor at 145° C. for 15 minutes to obtain a saponified mixture.

Then the saponified mixture was fed to a VTA modular vacuum distillation pilot plant consisting in three distillation columns or evaporators in series operated at the conditions shown in Table 2.

TABLE 2

Evaporation area and operation parameters of the VTA modular vacuum distillation pilot plant for the distillation of the saponified mixture of example 1.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 290 | 308 | 332 |
| Temperature condenser, ° C. | 22 | 150 | 150 |
| Vacuum, mbar | 1031 | 35 | 0.03 |

The saponified mixture was fed to Distiller I at the rate of 10 kg/h, leading to 1.3 kg/h of second distillate and a second residue fed to Distiller II, leading to 130 g/h of third distillate and a third residue fed to Distiller III, leading to 2.6 kg/h of fourth distillate and 5.9 kg/h of fourth residue comprising fatty acid soaps. Table 3 below shows the composition of the fourth distillate.

TABLE 3

Composition of the fourth distillate of example 1.

| Attribute | Fourth distillate |
|---|---|
| Total Cholesterol, % | 75.3 |
| Acid Number, ml | <0.1 |
| Loss on Drying, % | <0.1 |
| Sulfated Ash, % | <0.05 |
| Peroxide Value, meq/kg | <1 |
| Dioxins, Furans and Dioxin like PCBs, TEQ ppt (upper bound) | 0.937 |
| Total PCB (209 congeners), ppb (upper bound) | 6.07 |
| Total, PAH (13 PAH), ppb | 1.1 |
| 3-MCPD ester, ppb | 340 |
| Glycidol, ppb | 520 |
| Organochlorine Pesticides and Pyrethroides, ppb | Not detected |
| Organophosphorus Pesticides, ppb | Not detected |

The cholesterol recovery yield of Cholesterol in example 1 was 88.0%.

Example 2: Process for the Production of Cholesterol from a "Light Waste Residue"

120 kg of the first residue of example 1 was mixed with 21.6 kg of an aqueous solution of NaOH (50%) in an agitated pressure reactor at 145° C. for 15 minutes to obtain a saponified mixture.

Then the saponified mixture was fed to a VTA modular vacuum distillation pilot plant consisting in three distillation columns or evaporators in series operated at the conditions shown in Table 4.

TABLE 4

Evaporation area and operation parameters of the VTA modular vacuum distillation pilot plant for the distillation of the saponified mixture of example 2.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 290 | 309 | 333 |
| Temperature condenser, ° C. | 22 | 150 | 150 |
| Vacuum, mbar | 1030 | 4 | 0.03 |

The saponified mixture was fed to Distiller I at the rate of 10 kg/h, leading to 1.3 kg/h of second distillate and a second residue fed to Distiller II, leading to 1.0 kg/h of third distillate and a third residue fed to Distiller III, leading to 1.8 kg/h of fourth distillate and 5.9 kg/h of fourth residue comprising fatty acid soaps. Table 5 below shows the composition of the fourth distillate.

TABLE 5

Composition of the fourth distillate of example 2.

| Attribute | Fourth distillate |
|---|---|
| Total Cholesterol, % | 93.7 |
| Acid Number, ml | <0.1 |
| Loss on Drying, % | <0.1 |
| Sulfated Ash, % | <0.05 |
| Peroxide Value, meq/kg | <1 |
| Dioxins, Furans and Dioxin like PCBs, TEQ ppt (upper bound) | 0.892 |
| Total PCB (209 congeners), ppb (upper bound) | 7.28 |
| Total, PAH (13 PAH), ppb | 0.9 |
| 3-MCPD ester, ppb | 280 |
| Glycidol, ppb | 460 |
| Organochlorine Pesticides and Pyrethroides, ppb | Not detected |
| Organophosphorus Pesticides, ppb | Not detected |

The cholesterol recovery yield of Cholesterol in example 2 was 76.9%.

Example 3. Process for the Production of Cholesterol from a "Light Waste Residue" with a Dual Distillate Short Path Evaporator in Step (i)

1000 kg of the "light waste residue" shown in Table 1 was fed at a mass flow of 90 kg/h to an UIC dual distillate short path evaporator having an evaporator surface of 1 m² and a collector tray located at the middle of the condenser. The tray allows the collecting of the condensate from the upper half of condenser, "the upper condensate" separately from the condensate from the lower half of condenser, "the lower condensate" collected at the rate of 60 kg/h, was recirculated and contacted with the incoming "light waste residue "as shown in FIG. 1, leading to a total mass flow rate to distiller (i) of 150 kg/h. At continuous operation the upper condensate rate was 60 kg/h and the residue (or first residue) rate was 30 kg/h with a cholesterol concentration of 27.1%. The distillation was carried out at the temperature of 168° C. and at a vacuum of 0.04 mbar.

150 kg of the first residue was mixed with 25.9 kg of an aqueous solution of NaOH (50%) in an agitated pressure reactor at 140° C. for 15 minutes to obtain a saponified mixture.

Then the saponified mixture was fed to a VTA modular vacuum distillation pilot plant consisting in three distillation columns or evaporators in series operated at the conditions shown in Table 6.

TABLE 6

Evaporation area and operation parameters of the VTA modular vacuum distillation pilot plant for the distillation of the saponified mixture of example 3.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 290 | 310 | 330 |
| Temperature condenser, ° C. | 22 | 150 | 150 |
| Vacuum, mbar | 1025 | 5 | 0.03 |

The saponified mixture was fed to Distiller I at the rate of 10 kg/h, leading to 1.3 kg/h of second distillate and a second residue fed to Distiller II, leading to 1.2 kg/h of third distillate and a third residue fed to Distiller III, leading to 1.8 kg/h of fourth distillate and 5.7 kg/h of fourth residue comprising fatty acid soaps. Table 7 below shows the composition of the fourth distillate.

TABLE 7

Composition of the fourth distillate of example 3.

| Attribute | Fourth distillate |
|---|---|
| Total Cholesterol, % | 96.2 |
| Acid Number, ml | <0.1 |
| Loss on Drying, % | <0.1 |
| Sulfated Ash, % | <0.05 |
| Peroxide Value, meq/kg | <1 |
| Dioxins, Furans and Dioxin like PCBs, TEQ ppt (upper bound) | 0.567 |
| Total PCB (209 congeners), ppb (upper bound) | 1.53 |
| Total, PAH (13 PAH), ppb | <0.5 |
| 3-MCPD ester, ppb | <100 |
| Glycidol, ppb | <100 |
| Organochlorine Pesticides and Pyrethroides, ppb | Not detected |
| Organophosphorus Pesticides, ppb | Not detected |

The cholesterol recovery yield of Cholesterol in example 3 was 75.4%.

Example 4: Process for the Production of Cholesterol from a "Light Waste Residue"

100 kg of the first residue of example 1 was mixed with 17.3 kg of an aqueous solution of NaOH (50%) in an agitated pressure reactor at 143° C. for 15 minutes to obtain a saponified mixture.

Then the saponified mixture was fed to a VTA modular vacuum distillation pilot plant consisting in three distillation columns or evaporators in series operated at the conditions shown in Table 8.

TABLE 8

Evaporation area and operation parameters of the VTA modular vacuum distillation pilot plant for the distillation of the saponified mixture of example 4.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 292 | 308 | 331 |
| Temperature condenser, ° C. | 22 | 150 | 150 |
| Vacuum, mbar | 1030 | 34 | 0.03 |

The saponified mixture was fed to Distiller I at the rate of 10 kg/h, leading to 1.3 kg/h of second distillate and a second residue fed to Distiller II, leading to 290 g/h of third distillate and a third residue fed to Distiller III, leading to 2.7 kg/h of fourth distillate and 5.7 kg/h of fourth residue comprising fatty acid soaps. Table 9 below shows the composition of the fourth distillate.

TABLE 9

Composition of the fourth distillate of example 4.

| Attribute | Fourth distillate |
|---|---|
| Total Cholesterol, % | 81.6 |
| Acid Number, ml | <0.1 |
| Loss on Drying, % | <0.1 |
| Sulfated Ash, % | <0.05 |
| Peroxide Value, meq/kg | <1 |
| Dioxins, Furans and Dioxin like PCBs, TEQ ppt (upper bound) | 0.527 |
| Total PCB (209 congeners), ppb (upper bound) | 1.89 |

TABLE 9-continued

Composition of the fourth distillate of example 4.

| Attribute | Fourth distillate |
|---|---|
| Total, PAH (13 PAH), ppb | <0.5 |
| 3-MCPD ester, ppb | <100 |
| Glycidol, ppb | <100 |
| Organochlorine Pesticides and Pyrethroides, ppb | Not detected |
| Organophosphorus Pesticides, ppb | Not detected |

The cholesterol recovery yield of Cholesterol in example 4 was 95.6%.

Example 5. Process for the Production of Cholesterol from a "Heavy Waste Residue"

150 kg of a "heavy waste residue" of a traditional two-step short path molecular distillation process for the manufacture of omega-3 ethyl ester concentrates comprising 12.5% of cholesterol was mixed with 31.5 kg of an aqueous solution of NaOH (50%) in a stirred pressure reactor at 140° C. for 15 minutes to obtain a saponified mixture.

Then the saponified mixture was fed to a VTA modular vacuum distillation pilot plant consisting in three distillation columns or evaporators in series operated at the conditions shown in Table 10.

TABLE 10

Evaporation area and operation parameters of the VTA modular vacuum distillation pilot plant for the distillation of the saponified mixture of example 5.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 292 | 311 | 332 |
| Temperature condenser, ° C. | 22 | 150 | 150 |
| Vacuum, mbar | 1027 | 45 | 0.03 |

The saponified mixture was fed to Distiller I at the rate of 10 kg/h, leading to 1.8 kg/h of a first distillate and a first residue fed to Distiller II, leading to 410 g/h of a second distillate and a second residue fed to Distiller III, leading to 1.0 kg/h of a third distillate and 6.8 kg/h of a third residue comprising fatty acid soaps. Table 11 below shows the composition of the third distillate.

TABLE 11

Composition of the third distillate of example 5.

| Attribute | Third distillate |
|---|---|
| Total Cholesterol, % | 91.2 |
| Acid Number, ml | <0.1 |
| Loss on Drying, % | <0.1 |
| Sulfated Ash, % | <0.05 |
| Peroxide Value, meq/kg | <1 |
| Dioxins, Furans and Dioxin like PCBs, TEQ ppt (upper bound) | 0.548 |
| Total PCB (209 congeners), ppb (upper bound) | 1.62 |
| Total, PAH (13 PAH), ppb | 0.7 |
| 3-MCPD ester, ppb | <100 |
| Glycidol, ppb | <100 |
| Organochlorine Pesticides and Pyrethroides, ppb | Not detected |
| Organophosphorus Pesticides, ppb | Not detected |

The cholesterol recovery yield of Cholesterol in example 5 was 89.0%.

100 g of distillate 1 from Distiller I was evaporated in a rotary evaporator at 50 mbar and 101° C. 29.5 g of a residue was collected with a glycerin content of 99.4%.

Example 6: Concentrate of Free Fatty Acids 10.0 kg of the residue of fatty acid soaps from example 1 was dissolved in a stirred reactor with 30 kg of hot water and acidulated with 30 kg an aqueous solution of sulfuric acid at a concentration of 10%. Two phases were produced and the lower phase was discarded. The upper phase was washed with hot water, separated and dried under vacuum to obtain 9.2 kg of a mixture of free fatty acids.

Then the free fatty acid mixture was distillated in the VTA modular vacuum distillation pilot plant operating at the conditions set in Table 12, at a feed rate of 5 kg/h and obtaining a concentrate of fatty acids from the distillate of Distiller III at a rate of 1.9 kg/h. The analysis of Distiller III distillate is shown in Table 13.

TABLE 12

Evaporation area and operation parameters of the VTA modular vacuum distillation pilot plant in example 6.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 120 | 141 | 162 |
| Temperature condenser, ° C. | 25 | 25 | 25 |
| Vacuum, mbar | 10 | 0.04 | 0.01 |

TABLE 13

Composition of the free fatty acids from the distillate of Distiller III of example 6.

| | Ethyl ester concentrate (distillate of Evaporator C) |
|---|---|
| Eicosapentaenoic acid, as EE, % | 26.1 |
| Docosahexaenoic acid, as EE, % | 20.5 |
| Cholesterol, % | <0.1 |
| Color, Gardner | 1.5 |
| Totox | 3.1 |
| Absorbance at 233 nm | 0.33 |
| Acid Number, mg KOH/g | 190.1 |
| Oligomers and Glycerides, % | <0.5 |
| Trans-Fatty Acids, % | 0.2 |
| Lead (Pb), ppm | <0.001 |
| Cadmium (Cd), ppm | <0.001 |
| Mercury (Hg), ppm | <0.001 |
| Arsenic (As), ppm | <0.001 |
| Dioxins, Furans and Dioxin like PCBs, TEQ ppt (upper bound) | 0.417 |
| Total PCB (209 congeners), ppb (upper bound) | 0.27 |
| Total PAH (13 PAH), ppb | <0.5 |
| 3-MCPD ester, ppb | <100 |
| Glycidol, ppb | <100 |
| Organochlorine Pesticides and Pyrethroides, ppb | Not detected |
| Organophosphorus Pesticides, ppb | Not detected |

Example 7: Concentrate of Ethyl Esters 10.0 kg of the residue of fatty acid soaps from example 5 was dissolved in a stirred reactor with 30 kg of hot water and acidulated with 16 kg an aqueous solution of sulfuric acid with a concentration of 10%. Two phases were produced and the lower phase was discarded. The upper phase was washed with hot water, separated and dried under vacuum to obtain 9.2 kg of a mixture of free fatty acids.

The dry free fatty acids were esterified with ethanol to produce crude ethyl esters. 9 kg of the above free fatty acids were dissolved with 40 kg of ethanol and 1 kg of a 10% sulfuric acid solution in ethanol in a 70 liter glass reactor. The mixture was gently evaporated at 500 mbar until 90% of the ethanol was evaporated. Then 20 kg of water was added and 100 g of sodium hydroxide. The mixture was stirred for 5 min and then decanted for 30 min. The lower phase is discharged. 20 kg of water is added and the procedure is repeated. 9.7 kg of an oily phase was recovered which comprises crude ethyl esters.

Then the crude ethyl esters were distillated in the VTA modular vacuum distillation pilot plant operating at the conditions set in Table 14, at a feed rate of 5 kg/h and obtaining a concentrate of ethyl esters from the distillate of Distiller III at a rate of 1.2 kg/h. The analysis of Distiller III distillate is shown in Table 15.

TABLE 14

Evaporation area and operation parameters of the VTA modular vacuum distillation pilot plant in example 7.

| | Distiller I | Distiller II | Distiller III |
|---|---|---|---|
| Model | VD-125-20 Thin film distillation column | VK-83-6 Short Path distillation column | VK-83-6 Short Path distillation column |
| Area (m2) | 0.2 | 0.06 | 0.06 |
| Temperature jacket, ° C. | 120 | 136 | 152 |
| Temperature condenser, ° C. | 25 | 25 | 25 |
| Vacuum, mbar | 10 | 0.05 | 0.01 |

TABLE 15

Complete characterization of the concentrate of ethyl ester from example 7.

| | Ethyl ester concentrate (distillate of Distiller III) |
|---|---|
| Eicosapentaenoic acid, as EE, % | 23.6 |
| Docosahexaenoic acid, as EE, % | 57.9 |
| Cholesterol, % | <0.1 |
| Color, Gardner | 0.9 |
| Totox | 2.2 |
| Absorbance at 233 nm | 0.31 |
| Ethyl esters, % | >99 |
| Oligomers and Glycerides, % | <0.5 |
| Trans-Fatty Acids, % | 0.2 |
| Lead (Pb), ppm | <0.001 |
| Cadmium (Cd), ppm | <0.001 |
| Mercury (Hg), ppm | <0.001 |
| Arsenic (As), ppm | <0.001 |
| Dioxins, Furans and Dioxin like PCBs, TEQ ppt (upper bound) | 0.340 |
| Total PCB (209 congeners), ppb (upper bound) | 0.23 |
| Total PAHs (13 PAH), ppb | <0.5 |
| 2-MCPD ester, ppb | <100 |
| 3-MCPD ester, ppb | <100 |
| Glycidol, ppb | <100 |
| Organochlorine Pesticides and Pyrethroides, ppb | Not detected |
| Organophosphorus Pesticides, ppb | Not detected |
| Polybrominated biphenyls (7PBB), ppt | <0.885 |
| Polybrominated diphenyls ethers (24PBDE), ppt | <1.98 |
| Tetrabromobisphenol A (TBBPA), ppt | <4.81 |
| Hexabromocyclodocecane (3 HBCD), ppt | <0.0294 |
| Short chain chlorinated paraffins (SCCP), ppb | 3.86 |

TABLE 15-continued

Complete characterization of
the concentrate of ethyl ester from example 7.

|  | Ethyl ester concentrate (distillate of Distiller III) |
|---|---|
| Short chain chlorinated paraffins (MCCP), ppb | 5.56 |
| Organotin Compound (8 OTC), ppt | <21 |
| Toxaphene (Parlar Congeners), ppm | <0.08 |
| Plasticizers, ppm | Not detected |
| Organoleptic Test, odor (a) | 10 - Fruit (melon) |
| Organoleptic Test, flavor (a) | 10 - Nuts and Seeds (fresh nuts) |

Note
(a): Based on Larssen et al., Sensory description of marine oils through development of a sensory wheel and vocabulary, Food Research International, 106 (2018) 45-53.

The invention claimed is:

1. A process for producing from fish oil processing waste residues comprising cholesterol, a composition comprising over 75% in weight of cholesterol, comprising the steps:
   (a) contacting a fish oil processing waste residue comprising cholesterol with an aqueous solution comprising sodium hydroxide or potassium hydroxide, to obtain a saponified mixture,
   (b) subjecting the saponified mixture to a distillation step to obtain a first distillate and a first residue,
   (c) subjecting the first residue to a vacuum distillation step to obtain a second distillate and a second residue, and
   (d) subjecting the second residue to a vacuum distillation step to obtain a third distillate and a third residue, wherein the third distillate is a composition comprising over 75% in weight of cholesterol.

2. The process according to claim 1, wherein in step (a) the aqueous solution of sodium hydroxide or potassium hydroxide further comprises ethanol or methanol.

3. The process according to claim 1, wherein the third distillate of step (d) is subjected to prilling to obtain cholesterol prills.

4. The process according to claim 1, wherein the third residue of step (d) is acidified with a mineral acid to form a composition comprising from 20 to 60% in weight of omega-3 fatty acids, said composition comprising eicosapentaenoic acid, docosahexaenoic acid and docosapentaenoic acid.

5. The process according to claim 4, wherein the composition is subjected to molecular distillation to obtain a concentrate comprising from 40 to 90% in weigh of omega-3 fatty acids.

6. The process according to claim 4, wherein the composition comprising omega-3 fatty acids are esterified with ethanol to obtain a composition comprising ethyl esters of omega-3 fatty acids.

7. The process according to claim 6, wherein the composition comprising ethyl esters of omega-3 fatty acids is subjected to molecular distillation to obtain a concentrate comprising from 40 to 90% in weight of ethyl esters of omega-3 fatty acids.

8. A process for producing from fish oil processing waste residues comprising cholesterol, a composition comprising over 75% in weight of cholesterol, comprising the steps:
   (i) vacuum distilling a fish oil processing waste residue comprising cholesterol to obtain a first distillate and a first residue,
   (ii) contacting the first residue with an aqueous solution comprising sodium hydroxide or potassium hydroxide, to obtain a saponified mixture,
   (iii) subjecting the saponified mixture to a distillation step to obtain a second distillate and a second residue,
   (iv) subjecting the second residue to a vacuum distillation step to obtain a third distillate and a third residue, and
   (v) subjecting the third residue to a vacuum distillation step to obtain a fourth distillate and a fourth residue, wherein the fourth distillate is a composition comprising over 75% in weight of cholesterol.

9. The process according to claim 8, wherein the vacuum distilling the fish oil processing waste residue in step (i) is carried out in dual distillate short path evaporator.

10. The process according to claim 9, wherein the lower condensate fraction from the evaporator is contacted with the fish oil processing waste residue fed to the evaporator in step (i).

11. The process according to claim 8, wherein in step (ii) the aqueous solution of sodium hydroxide or potassium hydroxide further comprises ethanol or methanol.

12. The process according to claim 8, wherein the forth distillate of step (v) is subjected to prilling to obtain cholesterol prills.

13. The process according to claim 8, wherein the forth residue of step (v) is acidified with a mineral acid to form a composition comprising from 20 to 60% in weight of omega-3 fatty acids, said composition comprising eicosapentaenoic acid, docosahexaenoic acid and docosapentaenoic acid.

14. The process according to claim 13, wherein the composition is subjected to molecular distillation to obtain a concentrate comprising from 40 to 90% in weight of omega-3 fatty acids.

15. The process according to claim 13, wherein the composition comprising omega-3 fatty acids are esterified with ethanol to obtain a composition comprising ethyl esters of omega-3 fatty acids.

16. The process according to claim 15, wherein the composition comprising ethyl esters of omega 3 fatty acids is subjected to molecular distillation to obtain a concentrate comprising from 40 to 90% in weight of ethyl esters of omega-3 fatty acids.

* * * * *